United States Patent [19]

Mohring et al.

[11] 4,263,296
[45] Apr. 21, 1981

[54] COMBATING ARTHROPODS WITH 1,3-SUBSTITUTED-(1,2,3,4,5,6H)-TRIAZINE-2,4-DIONES

[75] Inventors: Edgar Mohring, Bergish Gladbach; Peter Stadler, Haan; Peter Roessler, Bergish Gladbach, all of Fed. Rep. of Germany

[73] Assignee: Bayer Aktiengesellschaft, Leverkusen, Fed. Rep. of Germany

[21] Appl. No.: 971,292

[22] Filed: Dec. 20, 1978

[30] Foreign Application Priority Data

Jan. 11, 1978 [DE] Fed. Rep. of Germany ....... 2801029

[51] Int. Cl.³ ........................................... A01N 43/64
[52] U.S. Cl. .................................... 424/249; 544/223
[58] Field of Search ......................... 544/223; 424/249

[56] References Cited

U.S. PATENT DOCUMENTS

| 3,035,055 | 5/1962 | Slezak et al. | 544/223 |
| 4,080,502 | 3/1978 | Seng et al. | 544/223 |
| 4,174,392 | 11/1979 | Mohring et al. | 544/223 |
| 4,174,445 | 11/1979 | Mohring et al. | 544/223 |

FOREIGN PATENT DOCUMENTS

| 1670668 | 12/1970 | Fed. Rep. of Germany . |
| 2460824 | 6/1976 | Fed. Rep. of Germany . |
| 2317283 | 2/1977 | France . |

OTHER PUBLICATIONS

Etienne et al., Bull. de la Soc. Chim. de France, pp. 1419-1424, nr. 5-6 (May–Jun.) 1975.

*Primary Examiner*—John M. Ford
*Attorney, Agent, or Firm*—Sprung, Felfe, Horn, Lynch & Kramer

[57] ABSTRACT

1,3-Substituted-(1,2,3,4,5,6H)-triazine-2,4-diones of the formula

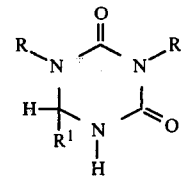

in which

R represents straight-chain, branched or cyclic alkyl with up to 20 carbon atoms which is optionally monosubstituted or polysubstituted by halogen, cyano, aryloxy, alkoxy or halogenoalkoxy, or represents phenyl or naphthyl, either of which is optionally monosubstituted or polysubstituted by halogen, CN, $C_1$–$C_4$-alkyl, monoalkylamino, dialkylamino, halogenoalkyl, phenoxy (which is optionally substituted by halogen and/or halogenoalkyl), alkoxy or halogenoalkoxy, or represents phenylsulphonyl which is optionally substituted by halogen, cyano, monoalkylamino, dialkylamino or alkoxy, or represents alkylsulphonyl which is optionally substituted by halogen or cyano and $R^1$ represents hydrogen, or represents straight-chain, branched or cyclic alkyl with up to 10 carbon atoms which is optionally substituted by halogen, alkoxy or cyano, or represents optionally substituted aryl, which possess arthropodicidal properties.

3 Claims, No Drawings

COMBATING ARTHROPODS WITH 1,3-SUBSTITUTED-(1,2,3,4,5,6H)-TRIAZINE-2,4-DIONES

The present invention relates to and has for its objects the provision of particular new 1,3-substituted-(1,2,3,4,5,6H)-triazine-2,4-diones which possess arthropodicidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is already known that triazine-2,4-diones have a good insecticidal activity. However, the action of these compounds is not satisfactory in all cases (see German Offenlegungsschrift (German Published Specification) No. 2,543,497).

The present invention now provides, as new compounds, the (1,2,3,4,5,6H)-triazine-2,4-diones of the general formula

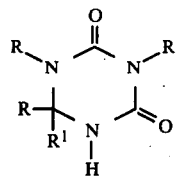

(I)

in which
R represents straight-chain, branched or cyclic alkyl with up to 20 carbon atoms which is optionally mono-substituted or polysubstituted by halogen, cyano, aryloxy, alkoxy or halogenoalkoxy, or represents phenyl or naphthyl, either of which is optionally monosubstituted or polysubstituted by halogen, CN, $C_1$-$C_4$ alkyl, monoalkylamino, dialkylamino, halogenoalkyl, phenoxy (which is optionally substituted by halogen and/or halogenoalkyl), alkoxy or halogenoalkoxy, or represents phenylsulphonyl which is optionally substituted by halogen, cyano, monoalkylamino, dialkylamino or alkoxy, or represents alkylsulphonyl which is optionally substituted by halogen or cyano and $R^1$ represents hydrogen, or represents straight-chain, branched or cyclic alkyl with up to 10 carbon atoms which is optionally substituted by halogen, alkoxy or cyano, or represents optionally substituted aryl (especially phenyl or naphthyl either of which is optionally substituted by halogen, cyano, alkyl with 1-10 carbon atoms, halogenoalkyl or alkoxy).

Preferably, $R^1$ represents hydrogen, methyl, ethyl, n-propyl, isopropyl, n-butyl, chlorohexyl or phenyl, and R represents methyl, ethyl, n-propyl, n-butyl, chlorohexyl, phenyl, 4-chlorophenyl, 3,4-dichlorophenyl, 4-methoxyphenyl, 2-trifluoromethylphenyl, 3-trifluoromethylphenyl, 3-chloro-4-trifluoromethylphenyl, 4-trifluoromethoxyphenyl, 4-p-phenoxyphenyl, 4-(3'-trifluoromethyl)-phenoxyphenyl, 4-fluorophenyl, 4-trifluoromethylphenyl or 4-chloro-3-trifluoromethylphenyl.

The following compounds according to the invention may be mentioned in particular: 1,3-di-p-chlorophenyl-(1,2,3,4,5,6H)-triazine-2,4-dione, 1,3-dimethyl-(1,2,3,4,5,6H)-triazine-2,4-dione, 1,3-diisopropyl(1,2,3,4,5,6H)-triazine-2,4-dione, 1,3-di-p-fluorophenyl-(1,2,3,4,5,6H)-triazine-2,4-dione, 1,3-bis-4-trifluoromethylphenyl(1,2,3,4,5,6H)-triazine-2,4-dione, 1,3-bis-4-chloro-3-trifluoromethylphenyl-(1,2,3,4,5,6H)-triazine-2,4-dione, 1,3-bis-3-chloro-4-trifluoromethylphenyl-(1,2,3,4,5,6H)-triazine-2,4-dione, 1,3-bis-6-chlorohexyl-(1,2,3,4,5,6H)-triazine-2,4-dione and 1,3-bis-4-phenoxyphenyl-(1,2,3,4,5,6H)-triazine-2,4-dione.

It was surprising and was not to be predicted that the hydrogenated triazine-2,4-diones according to the invention display an excellent inhibiting action on the development of insects.

The present invention also provides a process for the preparation of a compound of the formula (I) in which triazine-2,4-dione of the general formula

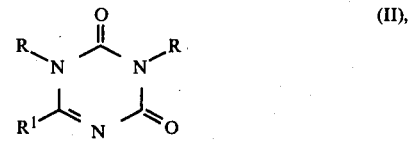

(II), in which
R and $R^1$ have the meanings stated above, is catalytically hydrogenated in a manner which is in itself known.

If 1,3-diphenyl-5-azauracil is used as the starting compound, the course of the reaction can be represented by the equation which follows:

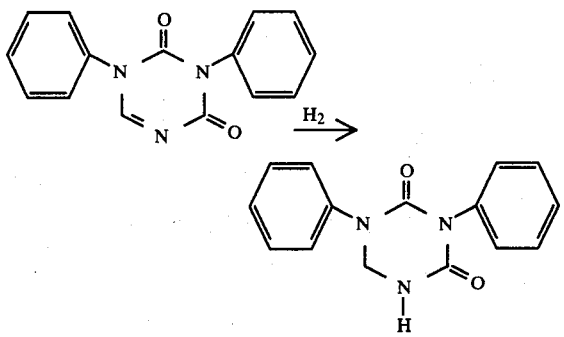

Triazine-2,4-diones used as the starting materials for the preparation of the compounds according to the invention are known from German Offenlegungsschrift (German Published Specification) No. 2,543,497 and can be obtained by processes analogous to the preparative processes indicated therein.

The preparation of the compounds according to the present invention is generally carried out using inert organic diluents. Examples of possible diluents are benzene, toluene, xylene, methylene chloride, chloroform, chlorobenzene, dibutyl ether, dioxane and, in particular, methanol, ethanol, isopropanol, acetone, methyl ethyl ketone, ethyl acetate and acetonitrile.

The reaction can be carried out under hydrogen pressures of between 1 and 200 bars, preferably between 20 and 100 bars, and at temperatures between 10° C. and 120° C., preferably between 40° C. and 100° C.

Catalysts which can be used in the process according to the invention are hydrogenation catalysts which predominantly contain metals of atomic number 23 to 29 in a reduced and/or oxidized form.

Examples of suitable catalysts are nickel catalysts or cobalt catalysts, such as supported nickel, supports which can be used being inorganic materials, such as kieselguhr, silicic acids, aluminas, silicates, aluminosilicates, montmorillonite, zeolites, spinels, dolomite, kaolin, magnesium silicates, zirconium oxide, iron oxide, zinc oxide, calcium carbonate, silicon carbide, aluminium phosphate, boron phosphate, asbestos or active charcoal, and organic catalyst supports which can be used being naturally occurring or synthetic compounds with a high molecular weight, such as silk, polyamides, polystyrenes, cellulose or polyurethanes, and it being possible for the supports to be in the form of balls, strands, filaments, cylinders or poly-yarns or in powdered form; Raney type catalysts, such as Raney nickel, W-1-, W-5-, W-6- and W-7-Raney nickel, as described by H. Adkins, J. Am. Chem. Soc. 69, 3039 (1974), Raney cobalt catalysts, Raney copper, Raney nickel/iron, Raney cobalt/nickel and Raney cobalt/iron; metal catalysts prepared by reducing nickel salts or cobalt salts, such as Urushibara nickel or nickel salts or cobalt salts reduced with metal-alkyl compounds, alkali metal hydrides, hydrazine, boranates or hydrogen boride; catalysts prepared by reduction of the metal oxides or metal oxide mixtures; and the metal oxides or oxide mixtures.

The catalysts can contain one or more of the following elements in amounts of up to 10% as accelerators: Li, Na, Ca, Ba, K, Ag, Be, La, Ce, V, Nb, Ta, Mo and W, and up to 1% of the elements Ru, Rh, Pd, Au, Ir and Pt.

Particularly suitable catalysts are: Raney nickel containing 90% by weight of Ni and 1% by weight of Fe, Ca and Na; Raney nickel/iron containing 5 to 30% by weight of Fe and 1% by weight of Ca and Na; Raney cobalt/iron containing 10-30% by weight of Fe; and palladium.

The catalyst necessary for the hydrogenation is generally employed in amounts of 10-100% by weight, relative to the compound to be hydrogenated.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., Meligethes aeneus, Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

To boost and supplement their spectrum of action, the active compounds according to the invention can, depending on the intended use, be combined with other insecticidal active compounds.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

When used in high concentrations, the compounds according to the invention also display a certain herbicidal action.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods, especially insects, which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The synthesis of the novel compounds is shown in the following preparative example:

EXAMPLE 1

General instruction:

10 g of the starting compound and 5 g of the hydrogenation catalyst were dissolved or suspended in 500 ml of methanol. This solution or suspension was hydrogenated in an autoclave under P bars at T degrees Celsius for N hours. The mixture was then allowed to cool and was let down and the catalyst was filtered off. The filtrate was concentrated to dryness. The substance which remained was investigated by thin layer chromatography and then appropriately recrystallized from chloroform or ethanol/acetone in the ratio of 1/1.

TABLE

| No. | Starting compound | Catalyst | N (hours) | P (bars) | T (°C.) | Yield (%) | Product | Melting point (°C.) |
|---|---|---|---|---|---|---|---|---|
| 1. | (structure) | Raney Ni | 4 | 150 | 100 | 93% | (structure) | 218° C. |
| 2. | " | Raney Ni | 1.5 | 60 | 75 | 91% | " | 217° C. |
| 3. | " | Pd-on-charcoal | 2 | 65 | 45 | 98% | " | 218° C. |
| 4. | (structure, Cl substituents) | Raney Ni | 2 | 90 | 95 | 96% | (structure, Cl substituents) | 173° C. |
| 5. | (structure, CH₃ substituents) | Raney Ni | 2 | 100 | 80 | 86% | (structure, CH₃ substituents) | 169° C. |
| 6. | (structure, CF₃ substituents) | Raney Ni | 2 | 70 | 70 | 95% | (structure, CF₃ substituents) | 143° C. |

The activity of the compounds of this invention is illustrated by the following examples wherein the compounds according to the present invention are each identified by the number (given in brackets) from Example 1.

In the test examples which follow, which relate to the development-inhibiting action of the active compounds, the morphological changes, such as half-pupated insects, incompletely slipped larvae or caterpillars, defective wings, pupal cuticula in imagos, and the like, were rated as malformations over the entire stated development of the test insects. The sum of the morphological malformations, together with the insects killed during shedding or during metamorphosis was determined as a percentage of the total number of test insects employed.

EXAMPLE 2

Development-inhibiting action/Laphygma caterpillar test

Test insects: *Laphygma frugiperda* (caterpillars)
Feed: 1 cm thick disc of 3 cm diameter, of an air-dried artificial feed based on shredded beans, yeast, vitamin mixture, leaf powder, agar and preservative
Solvent: 10 parts by weight of acetone
Emulsifier: 1 part by weight of alkylaryl polyglycol ether To produce a suitable preparation of active compound, 2 parts by weight of active compound were mixed with the stated amounts of solvent and emulsifier and with sufficient water to give a 1% strength mixture, which was diluted with water to the desired concentration.

Each test insect was placed on a separate feed disc moistened with 1.5 ml of active compound preparation of the desired concentration, and was observed until the imago slipped.

As a control, test insects were each placed on separate feed discs moistened with 1.5 ml of a mixture of solvent, emulsifier and water of the corresponding concentration and observed until the imago slipped.

In this test compound 4 showed a superior action compared to the prior art.

EXAMPLE 3

Development-inhibiting action/ingestion test
Test insects: *Plutella maculipennis* (caterpillars in the 4th stage of development)
Number of test insects: 20 specimens
Test insects: *Phaedon cochleariae* (larvae in the 4th stage of development)
Number of test insects: 20 specimens
Feed plants: Cabbage plants (*Brassica olearacea*)
Solvent: 10 parts by weight of acetone
Emulsifier: 1 part by weight of alkylaryl polyglycol ether To produce a suitable preparation of active compound, 2 parts by weight of active compound were mixed with the stated amounts of solvent and emulsifier and with sufficient water to give a 1% strength mixture, which has diluted with water to the desired concentration.

The test insects were fed with leaves of the feed plants, which were provided with a uniform spray covering of the active compound preparation in such a way that the desired concentration of active compound (amount of active compound per unit surface area) was obtained on the leaves, until the imago developed.

As a control, leaves coated only with a mixture of solvent, emulsifier and water of the corresponding concentration were used as the feed.

In this test compounds 4 and 6 showed a superior action compared to the prior art.

EXAMPLE 4

Development-inhibiting action/*Aedes aegypti* test

Test insects: *Aedes aegypti* (larvae in the 3rd stage of development)

Number of test insects: 20 specimens

Solvent: 10 parts by weight of acetone

Emulsifier: 1 part by weight of alkylaryl polyglycol ether

To produce a suitable preparation of active compound, 2 parts by weight of active compound were mixed with the stated amounts of solvent and emulsifier and with sufficient water to produce a mixture containing 100 ppm, which was diluted with water to the desired concentration.

The test insects were introduced into 90 ml of an active compound preparation of the desired concentration and were observed until the imago slipped. As a control, test insects were introduced into a mixture of solvent, emulsifier and water of the corresponding concentration and observed until the imago slipped.

In this test compound 4 and 6 showed a superior action compared to the prior art.

EXAMPLE 5

Development-inhibiting action/contact test

Test insect: *Dysdercus intermedius (larvae in the* 3rd stage of development)

Number of test insects: 10 specimens

Feed: Cotton seeds (*Cossypium hirsutum*)

Solvent: 10 parts by weight of acetone

Emulsifier: 1 part by weight of alkylaryl polyglycol ether

To produce a suitable preparation of active compound, 2 parts by weight of active compound were mixed with the stated amounts of solvent and emulsifier and with sufficient water to give a 1% strength mixture, which was diluted with water to the desired concentration.

The test insects were dipped for 3 seconds into the active compound preparation of the desired concentration and were then kept in cages and fed with untreated cotton seeds and water.

As a control, insects dipped only into a mixture of solvent, emulsifier and water of the corresponding concentration were kept, and fed in the same manner.

In this test compound 1 showed a superior action compared to the prior art. It will be appreciated that the instant specification and examples are set forth by way of illustration and not limitation, and that various modifications and changes may be made without departing from the spirit and scope of the present invention.

We claim:

1. An arthropodical composition containing as active ingredient an arthropodicidally effective amount of a compound of the formula

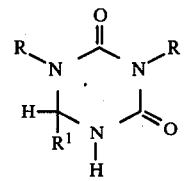

in which
R is methyl, ethyl, n-propyl, n-butyl, chlorohexyl, phenyl, 4-chlorophenyl, 3,4-dichlorophenyl, 4-methoxyphenyl, 2-trifluoromethylphenyl, 3-trifluoromethylphenyl, 3-chloro-4-trifluoromethylphenyl, 4-p-phenoxyphenyl, 4-(3'-trifluoromethyl)-phenoxyphenyl, 4-fluorophenyl, 4-trifluoromethylphenyl or 4-chloro-3-trifluoromethylphenyl, and
$R^1$ represents hydrogen, methyl, ethyl, n-propyl, isopropyl, n-butyl, chlorohexyl or phenyl
in admixture with a diluent.

2. A method of combating arthropods which comprises applying to arthropods, or to a habitat thereof, an arthropodicidally effective amount of a compound of the formula

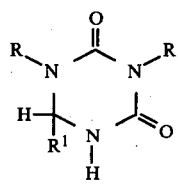

in which
R is methyl, ethyl, n-propyl, n-butyl, chlorohexyl, phenyl, 4-chlorophenyl, 3,4-dichlorophenyl, 4-methoxyphenyl, 2-trifluoromethylphenyl, 3-trifluoromethylphenyl, 3-chloro-4-trifluoromethylphenyl, 4-p-phenoxyphenyl, 4-(3'-trifluoromethyl)-phenoxyphenyl, 4-fluorophenyl, 4-trifluoromethylphenyl or 4-chloro-3-trifluoromethylphenyl, and
$R^1$ represents hydrogen, methyl, ethyl, n-propyl, isopropyl, n-butyl, chlorohexyl or phenyl.

3. The method according to claim 2, in which said compound is
1,3-di-phenyl-(1,2,3,4,5,6H)-triazine-2,4-dione,
1,3-di-p-chlorophenyl-(1,2,3,4,5,6H)-triazine-2,4-dione,
1,3-dimethyl-(1,2,3,4,5,6H)-triazine-2,4-dione or
1,3-bis-3-trifluoromethylphenyl-(1,2,3,4,5,6H)-triazine-2,4-dione.

* * * * *